US00PP27403P2

(12) United States Plant Patent
Lubbers

(10) Patent No.: US PP27,403 P2
(45) Date of Patent: Nov. 22, 2016

(54) ***SALIX* PLANT NAMED 'LUBBERS ZWART'**

(50) Latin Name: *Salix chaenomeloides*
Varietal Denomination: Lubbers Zwart

(71) Applicant: Howard L. Lubbers, Holland, MI (US)

(72) Inventor: Howard L. Lubbers, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 14/545,746

(22) Filed: Jun. 15, 2015

(51) Int. Cl.
*A01H 5/00* (2006.01)

(52) U.S. Cl.
USPC ..... Plt./226

(58) Field of Classification Search
USPC ..... Plt./226, 216
CPC ..... A01H 5/00; A01H 5/04
See application file for complete search history.

*Primary Examiner* — Kent L Bell
(74) *Attorney, Agent, or Firm* — C. A. Whealy

(57) ABSTRACT

A new and distinct cultivar of *Salix* plant named 'Lubbers Zwart', characterized by its upright to outwardly spreading plant habit; tall, strong and straight stems; freely branching habit; freely flowering habit; and dark grey-colored catkins.

1 Drawing Sheet

Botanical designation: *Salix chaenomeloides.*
Cultivar denomination: 'LUBBERS ZWART'.

BACKGROUND OF THE INVENTION

The present Invention relates to a new and distinct *Salix* plant, botanically known as *Salix chaenomeloides*, commonly referred to as Giant Pussy Willow, commercially used as an ornamental shrub and cut flower and hereinafter referred to by the name 'Lubbers Zwart'.

The new *Salix* plant is a naturally-occurring branch mutation of an unnamed selection of *Salix chaenomeloides*, not patented. The new *Salix* plant was discovered and selected by the Inventor in early 2008 on a single plant of the mutation parent in an outdoor cut flower nursery in Allegan County, Mich.

Asexual reproduction of the new *Salix* plant by hardwood cuttings in Holland Mich. since April, 2008, has shown that the unique features of this new *Salix* plant are stable and reproduced true to type in successive generations of asexual reproduction.

SUMMARY OF THE INVENTION

The following traits have been repeatedly observed and are determined to be the unique characteristics of 'Lubbers Zwart'. These characteristics in combination distinguish 'Lubbers Zwart' as a new and distinct *Salix* plant:

1. Upright to outwardly spreading plant habit.
2. Tall, strong and straight stems.
3. Freely branching habit.
4. Freely flowering habit.
5. Dark grey-colored catkins.

Plants of the new *Salix* differ from plants of the mutation parent in catkin color as plants of the mutation parent have lighter grey-colored catkins than plants of the new *Salix.*

Plants of the new *Salix* can be compared to plants of other selections of *Salix chaenomeloides* known to the Inventor. Plants of the new *Salix* differ primarily from plants of other selections of *Salix chaenomeloides* known to the Inventor in catkin color as plants of other selections of *Salix chaenomeloides* known to the Inventor have lighter grey-colored catkins than plants of the new *Salix.*

BRIEF DESCRIPTION OF THE PHOTOGRAPH

The accompanying colored photograph illustrates the overall appearance of the new *Salix* plant showing the colors as true as it is reasonably possible to obtain in colored reproductions of this type. Colors in the photograph may differ slightly from the color values cited in the detailed botanical description which accurately describe the colors of the new *Salix* plant.

The photograph comprises a side perspective view of a typical flowering stem of plant of 'Lubbers Zwart'.

DETAILED BOTANICAL DESCRIPTION

Plants of the new *Salix* have not been observed under all possible combinations of environmental conditions and cultural practices. The phenotype may vary somewhat with variations in environmental conditions such as temperature and light intensity, without, however, any variance in genotype. The aforementioned photograph, following observations and measurements describe plants grown in one-gallon containers during the spring in an outdoor nursery in Grand Haven, Mich. and under cultural practices typical of commercial *Salix* production. During the production of the plants day temperatures ranged from 18° C. to 27° C. and night temperatures ranged from 5° C. to 10° C. Plants were one year old when the photograph was taken and two years old when the description was taken. In the following description, color references are made to The Royal Horticultural Society Colour Chart, 1995 Edition, except where general terms of ordinary dictionary significance are used.

Botanical classification: *Salix chaenomeloides* 'Lubbers Zwart'.

Parentage: Naturally-occurring branch mutation of an unnamed selection of *Salix chaenomeloides*, not patented.

Propagation:

*Type*.—By hardwood cuttings.

*Time to initiate roots*.—About ten days at temperatures about 25° C.

*Root description*.—Fine to medium in thickness; white to brown in color.

*Rooting habit*.—Freely branching; medium density.

Plant description:

*Plant form*.—Upright somewhat outwardly spreading shrub that can also be used as cut flowers.

*Growth habit*.—Vigorous growth habit; rapid growth rate.

*Branching habit*.—Freely branching habit; about eight basal branches develop per plant; pinching enhances lateral branch development.

*Plant height*.—About 3.05 meters to 3.66 meters.

*Plant width* (*spread*).—About 2.44 meters to 3.05 meters.

*Basal branches*.—Length: About 42 cm. Diameter: About 5.5 mm to 11 mm. Internode length: About 2.2 cm to 2.7 cm. Strength: Strong, straight. Aspect: Upright to outwardly. Texture, developing branches: Slightly pubescent. Texture, developed branches: Smooth, glossy, glabrous. Color, developing branches: Close to 144A becoming closer to 165A with development. Color, developed branches: Depending on orientation, close to between 175A and 178A or close to 152A.

Leaf description:

*Arrangement*.—Alternate; simple.

*Length*.—About 6 cm to 8.5 cm.

*Width*.—About 2 cm to 3 cm.

*Shape*.—Lanceolate.

*Apex*.—Acute.

*Base*.—Cuneate.

*Margin*.—Serrulate to crenate.

*Texture, upper surface*.—Smooth to slightly pubescent.

*Texture, lower surface*.—Densely pubescent.

*Venation pattern*.—Pinnate.

*Color*.—Developing leaves, upper surface: Close to 137C. Developing leaves, lower surface: Close to 138B. Fully expanded leaves, upper surface: Close to 137A; venation, close to 145A. Fully expanded leaves, lower surface: Close to 139B; venation, close to 145C.

*Petioles*.—Length: About 5 mm. Diameter: About 1.5 mm. Texture, upper and lower surfaces: Smooth, glabrous. Color, upper and lower surfaces: Close to 145C.

Flower description:

*Flower type and habit*.—Fuzzy upright catkins alternately arranged on the primary branches; freely flowering with about 23 catkins per primary branch.

*Natural flowering season*.—Plants flower during the early spring in Grand Haven, Mich.; leaves develop after catkin development; flowers not persistent.

*Fragrance*.—None detected.

*Catkin length*.—About 1.6 cm to 4.5 cm.

*Catkin diameter*.—About 9 mm to 10.5 mm.

*Bud scale color*.—Close to 166A.

*Catkin color, developing*.—Close to 145A overlain with close to 155B and 51B.

*Catkin color, fully developed*.—Close to 54A overlain with close to 202A giving a dark grey-colored appearance.

*Reproductive organs*.—Stamens: Anther shape: Oblong. Anther length: Less than 0.5 mm. Anther color: Close to 7A. Pollen amount: Moderate. Pollen color: Close to 7A. Pistils: None observed.

Pathogen & pest resistance: Plants of the new *Salix* have not been observed to be resistant to pathogens and pests common to *Salix* plants.

Garden performance: Plants of the new *Salix* have been observed have good garden performance and to tolerate rain, wind and to be hardy to at least USDA Hardiness Zone 6.

It is claimed:

1. A new and distinct *Salix* plant named 'Lubbers Zwart' as illustrated and described.

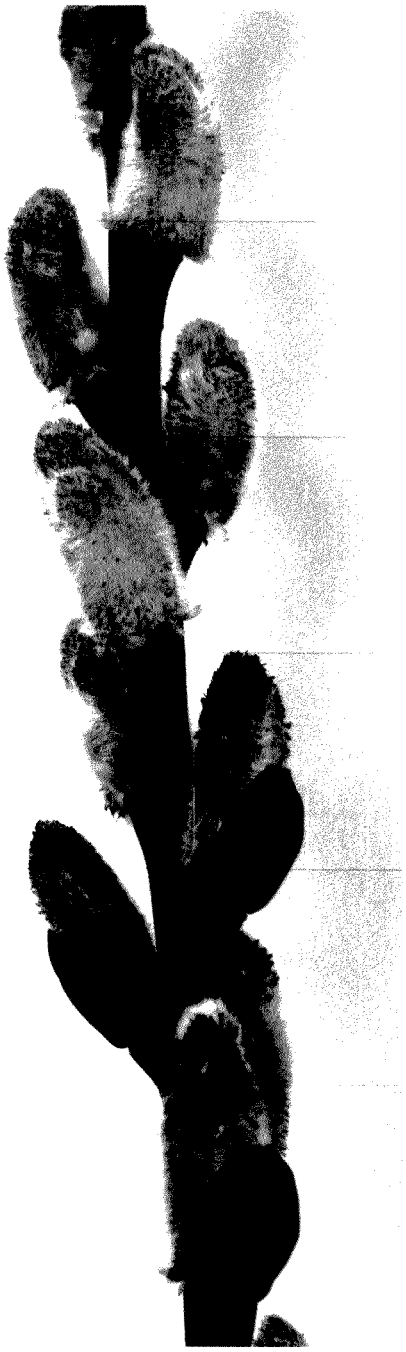

* * * * *